United States Patent [19]

Ascione

[11] Patent Number: 5,741,480

[45] Date of Patent: Apr. 21, 1998

[54] SELF-TANNING COSMETIC COMPOSITIONS

[75] Inventor: Jean-Marc Ascione, Paris, France

[73] Assignee: Société L'Oréal S.A., Paris, France

[21] Appl. No.: 629,227

[22] Filed: Apr. 8, 1996

[30] Foreign Application Priority Data

Apr. 7, 1995 [FR] France .................. 95-04192

[51] Int. Cl.$^6$ .................. A61K 7/42; A61K 7/00; A61K 31/695

[52] U.S. Cl. .................. 424/59; 424/60; 424/400; 424/401; 514/63

[58] Field of Search .................. 424/59, 60, 400, 424/401; 514/63

[56] References Cited

U.S. PATENT DOCUMENTS 5,232,688 8/1993 Ziegler et al. .................. 424/59

FOREIGN PATENT DOCUMENTS 0547864 6/1993 European Pat. Off. .
0576189 12/1993 European Pat. Off. .
2698267 5/1994 France .
94/422418 10/1994 WIPO .

Primary Examiner—Shelley A. Dodson
Attorney, Agent, or Firm—Burns, Doane, Swecker & Mathis, L.L.P.

[57] ABSTRACT

The present invention relates to artificial tanning cosmetic compositions comprising, in a cosmetically acceptable water-in-silicone emulsion, DHA, at least one mono- or dihydric alcohol and a silicone-containing polydimethylsiloxane emulsifying agent of the following formula (I) or (II):

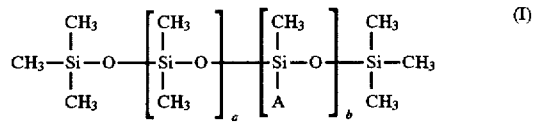

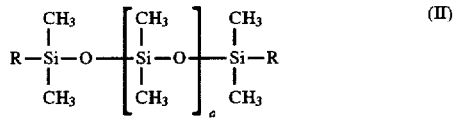

24 Claims, No Drawings

SELF-TANNING COSMETIC COMPOSITIONS

The present invention relates to novel cosmetic compositions for topical use more particularly intended for the artificial tanning and/or bronzing of the skin (compositions referred to more simply hereinbelow as self-tanning compositions), as well as to their use in the abovementioned cosmetic application. Even more precisely, the invention relates to self-tanning compositions with improved activity and stability, in the form of specific emulsions of water-in-silicone type (cosmetically acceptable support) and comprising, as self-tanning agent, dihydroxyacetone.

It is known that dihydroxyacetone, or DHA, is a particularly advantageous product which is commonly used in cosmetics as an agent for the artificial tanning of the skin; when applied to the skin, in particular to the face, this product makes it possible to obtain a tanning or bronzing effect similar in appearance to that which might result from prolonged exposure to the sun (natural tanning) or under a UV lamp. Such a use also has the advantage of entirely avoiding the risks of skin reaction generally attached to the abovementioned prolonged exposures (erythema, burns, loss of elasticity, appearance of wrinkles, premature ageing of the skin, and the like).

For various reasons associated in particular with greater comfort of use (softness, emollience, ease of application), the current self-tanning compositions are usually in the form of an emulsion of oil-in-water type (that is to say a support consisting of an aqueous dispersing continuous phase and an oily dispersed discontinuous phase) into which has been introduced, at various concentrations, dihydroxyacetone which, on account of its hydrophilic nature, is found in the aqueous phase of the emulsion.

However, one of the drawbacks of the self-tanning compositions known to date and belonging to the above type (O/W emulsion containing DHA) is that the intensity of the coloration obtained on the skin and/or the speed with which this coloration develops may still appear to be insufficient.

Moreover, another difficulty lies in the fact that DHA has an unfortunate tendency, which is more or less pronounced depending on the nature of the medium in which it is formulated, to degrade over time, thereby giving rise to storage and/or preservation problems which are generally reflected in the long run by an undesirable yellowing of the compositions which contain it.

The aim of the present invention is, in particular, to solve the above problems, by proposing novel DHA-based emulsions which are of improved self-tanning activity and/or efficiency on the skin (intensity and staying power), along with, moreover, excellent stability.

Thus, after considerable research conducted in this matter, the Applicant has now found, entirely unexpectedly and surprisingly, that by formulating DHA in water-in-silicone emulsions containing, on the one hand, a specific silicone-containing emulsifying agent, and, on the other hand, a mono- or dihydric alcohol, the quality of coloration of the skin in terms of intensity and uniformity, and the stability of the DHA, could be improved substantially.

This discovery forms the basis of the present invention.

Thus, in accordance with one of the subjects of the present invention, novel cosmetic compositions intended for the artificial taming of the skin are now proposed, these compositions comprising, in a cosmetically acceptable support of water-in-silicone emulsion type, dihydroxyacetone as self-tanning agent, and which are essentially characterized in that they also contain:

at least one mono- or dihydric alcohol, at least one silicone-containing emulsifying agent consisting of a polydimethylsiloxane of formula (I) or (II), optionally dispersed in a volatile polydimethylsiloxane,

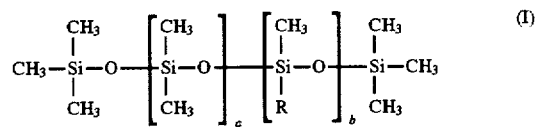

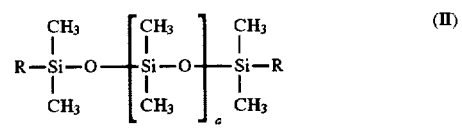

in which formulae (I) and (II):

$1 \leq a \leq 500$ (a being an integer)

$1 \leq b \leq 100$ (b being an integer)

R represents a radical:

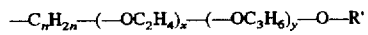

in which R' represents H or a linear or branched $C_1$–$C_{12}$ alkyl radical, and:

$0 \leq x \leq 50$ (x being an integer)

$0 \leq y \leq 50$ (y being an integer)

$x+y \geq 1$ $2 \leq n \leq 12$ (n being an integer)

Besides their improved intrinsic self-tanning properties, the compositions in accordance with the invention have very good stability over time. They furthermore have the advantage, which is very much appreciated commercially, of being able to be transparent when the refractive index i of the aqueous phase is close to that of the silicone-containing continuous phase, namely when:

{i silicone-containing phase—i aqueous phase} ≤ 0.01.

Other characteristics, aspects and advantages of the invention will become apparent on reading the detailed description which follows.

The dihydroxyacetone, or DHA, is present in the water-in-silicone emulsion according to the invention in sufficient proportions to impart to the skin, after application, a coloration similar to the coloration obtained after natural tanning. It is thus generally present in proportions of between 0.5 and 10% by weight relative to the total weight of the emulsion, and preferably of between 1 and 7% by weight relative to the total weight of the composition.

The silicone or silicones constituting the continuous phase of the emulsion are generally linear or cyclic, volatile silicones. Preferably, they are linear or cyclic volatile polydimethylsiloxanes. Such polydimethylsiloxanes are, for example, cyclomethicone sold under the trade name "Silbione oil 70 047 V 2" by Rhône-Poulenc.

The silicones are generally present in the compositions according to the invention in a proportion of between 1 and 50%, preferably of between 5 and 25%, by weight relative to the total weight of the composition.

According to an essential characteristic of the present invention, the compositions in accordance with the invention also comprise a third compound which is a specific silicone-containing emulsifying agent of high molecular weight consisting of a polydimethylsiloxane bearing polyoxyethylene and/or polyoxypropylene chains grafted onto the main chain, this emulsifying agent having the following structure (I) or (II):

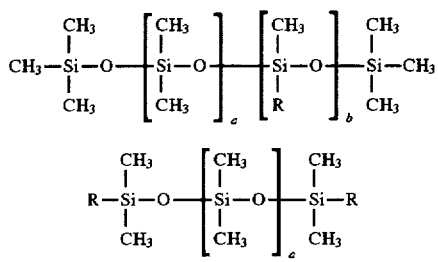

in which formulae (I) and (II):

$1 \leq a \leq 500$ (a being an integer)
$1 \leq b \leq 100$ (b being an integer)
R represents a radical:

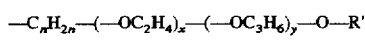

in which R' represents H or a linear or branched $C_1-C_{12}$ alkyl radical, and:

$0 \leq x \leq 50$ (x being an integer)
$0 \leq y \leq 50$ (y being an integer)
$x+y \geq 1$
$2 \leq n \leq 12$ (n being an integer)

Preferably, according to the invention, silicone-containing emulsifying agents having at least one, and even more preferably all, of the following characteristics are used:

$2 \leq a \leq 450$
$2 \leq b \leq 40$
$1 \leq x \leq 30$
$0 \leq y \leq 30$
$y \leq x$ Examples of linear or branched $C_1-C_{12}$ alkyl radicals R' which may be mentioned in particular are the methyl, ethyl, n-propyl, isopropyl, n-butyl, isobutyl, pentyl and hexyl radicals.

According to the present invention, R' preferably represents hydrogen.

In a preferred embodiment of the invention, the silicone-containing emulsifying agent is the polydimethylsiloxane corresponding to the following formula:

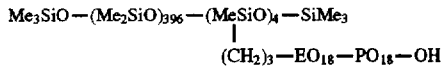

in which EO represents an ethylene oxide unit and PO represents a propylene oxide unit.

By way of example of a silicone-containing emulsifying agent which is particularly suitable for carrying out the present invention, mention may be made of the polydimethylsiloxane sold under the trade name "Silicone Q₂3225C" by the company Dow Corning.

The silicone-containing emulsifying agent or agents are generally present in the compositions according to the invention in a proportion of between 0.1 and 20% by weight, preferably of between 0.5 and 10% by weight, relative to the total weight of the composition.

According to another essential characteristic of the present invention, the compositions in accordance with the invention also comprise at least one mono- or dihydric alcohol, preferably a dihydric alcohol.

As monoalcohols which may be used according to the invention, mention may be made of ethanol and isopropanol.

As dihydric alcohols, mention may be made most particularly of isopentyldiol, butylene glycol or propylene glycol. According to a particularly preferred embodiment of the invention, propylene glycol is used as dihydric alcohol.

Preferably, the mono- or dihydric alcohol or alcohols are present in the composition in a proportion of at least 2%, and even more preferably in a proportion of between 10 and 50% by weight, relative to the total weight of the composition.

The self-tanning compositions in accordance with the invention may be in the form of creams, milks, gels, cream-gels, fluid lotions, in particular vaporizable fluid lotions, or any other form generally used in cosmetics, in particular a form usually suitable for self-tanning cosmetic compositions.

As indicated above, on account of its water-soluble nature, dihydroxyacetone is present in the aqueous phase of the emulsions according to the invention.

Among the standard cosmetic adjuvants which may be contained in the aqueous phase and/or in the silicone-containing phase of the emulsions in accordance with the invention (depending on their water-soluble and/or lipo-soluble nature), mention may be made in particular of ionic or nonionic thickeners, softeners, antioxidants, opacifiers, stabilizers, emollients, insect repellants, organic sunscreens active in the UV-A and/or UV-B range, photoprotective mineral pigments and nanopigments, moisturizers, vitamins, fragrances, preserving agents, fillers, sequestering agents, dyes or any other ingredient usually used in the field of self-tanning products.

Obviously, a person skilled in the art will take care to choose this or these possible complementary compounds and/or their amounts such that the advantageous properties intrinsically attached to the emulsion in accordance with the invention are not, or are substantially not, detrimentally affected by the addition or additions envisaged.

Another subject of the present invention consists of the use of compositions as defined above as, or for the manufacture of, cosmetic compositions for the artificial tanning and/or bronzing of the skin. As mentioned above, the compositions may then be conditioned in the form of creams, milks, cream gels or alternatively fluid lotions, in particular vaporizable fluid lotions, or any other suitable form.

Another subject of the present invention lies in a process for the cosmetic treatment of the skin which is intended to artificially tan and/or bronze it and which consists essentially in applying an effective amount of a cosmetic composition as defined above to the skin.

Concrete, but in no way limiting, examples intended to illustrate the invention will now be given.

In all of the examples which follow, the amounts are expressed as % by weight relative to the total weight of the composition.

EXAMPLE 1

The Applicant evaluated, by means of a comparative test, the skin coloration obtained with two compositions each containing 5% of DHA. A first composition (1), namely a water-in-silicone emulsion in accordance with the invention, and a second composition (2), namely a niosome-containing O/W emulsion representative of the state of the art, were thus prepared.

| Composition (1): | |
|---|---|
| A: | |
| polydimethylsiloxane sold under the trade name "Silicone Q₂3225C" by Dow Corning | 10% |
| polydimethylsiloxane sold under the trade name "Silbione oil 70 047 V 2" by Rhône-Poulenc | 7% |
| B: | |
| dihydroxyacetone | 5% |
| anhydrous dextrose | 2% |
| propylene glycol | 39% |
| demineralized water | qs 100% |
| Composition (2): | |
| A: Dispersed nonionic lipid vesicles (niosomes): | |
| cetyl alcohol polyglycerolated with 3 mol of glycerol (Chimexane NL from Chimex) | 3.8% |
| cholesterol | 3.8% |
| monosodium stearoyl glutamate (acylglutamate HS 11 from Ajinomoto) | 0.4% |
| D: Dispersed liquid oily phase: | |
| liquid petrolatum | 8% |
| cyclomethicone | 5% |
| B: Water: | 8% |
| E: Aqueous gelling phase: | |
| hydroxyethylcellulose | 0.5% |
| preserving agents | qs |
| water | 30% |
| C: Aqueous dispersing phase: | |
| glycerol | 2% |
| dihydroxyacetone | 5% |
| water | qs 100% |

Composition (1) was prepared as follows: B was poured slowly into A with gentle Moritz stirring at 1500 rpm and at room temperature. The composition was then left stirring for about 10 min. the speed gradually being increased to about 4500 rpm.

Composition (2) was itself prepared in the following way: phase E was prepared by dispersion of the gelling agent in the water at 60° C. with stirring. Phase A and phase B were then heated separately at 80°–85° C. until homogenized. B was then added to A with vigorous Turrax stirring. When the mixture (A+B) had returned to room temperature, phase C was added, followed by phase D. Lastly, phase E was added with gentle stirring.

For these two compositions thus prepared, the intensity of coloration attached to them after a certain time T, i.e. $\Delta L_T$, was then determined. The intensity of coloration was measured according to the following method: these formulations were applied to areas of 4.5 cm×4.5 cm, at a rate of 2 mg/cm² of skin, onto the backs of 5 human models, and colorimetric measurements were then taken using a Minolta CR 200 colorimeter 1 h 30, 3 h, 5 h and 24 h after application of the products.

The average ΔL results are collated in Table (I) below:

TABLE (I)

| | Composition (1) | Composition (2) |
|---|---|---|
| ΔL 1 h 30 | 1.2 | 0.3 |
| ΔL 3 h | 1.9 | 1.1 |
| ΔL 5 h | 3.2 | 2.4 |
| ΔL 24 h | 4.2 | 3.2 |

These results show clearly that a faster and significantly more intense rise in coloration is obtained with the composition in accordance with the invention.

EXAMPLE 2

The aim of this example is to show the critical nature of the silicone-containing emulsifying agent in accordance with the invention. Two compositions, a composition (3) in accordance with the invention and a comparative composition (4) not containing the silicone-containing emulsifying agent as defined in the present invention but another silicone-containing emulsifying agent, were prepared according to the procedure used for composition (1) of Example 1.

| Composition (3): | |
|---|---|
| polydimethylsiloxane sold under the trade name "Silicone Q₂3225C" by Dow Corning | 10% |
| polydimethylsiloxane sold under the trade name "Silbione oil 70 047 V 2" by Rhône-Poulenc | 7% |
| dihydroxyacetone | 5% |
| anhydrous dextrose | 2% |
| propylene glycol | 20% |
| preserving agents | qs |
| demineralized water | qs 100% |
| Composition (4): | |
| cetyldimethicone copolyol sold under the trade name "Silicone Abil EM 90" by Goldschmidt | 1% |
| polydimethylsiloxane sold under the trade name "Silbione oil 70 047 V 2" by Rhône-Poulenc | 16% |
| dihydroxyacetone | 5% |
| anhydrous dextrose | 2% |
| propylene glycol | 20% |
| preserving agents | qs |
| demineralized water | qs 100% |

For these two compositions thus prepared, the intensity of coloration was measured according to the following method: these formulations were applied to areas of 2.5 cm×2.5 cm, at a rate of 2 mg/cm² of skin, to the inner forearms of 3 human models, namely $M_1$, $M_2$ and $M_3$, and colorimetric measurements were then taken using a Minolta CM 1000 colorimeter, 3 h after application of the products. The results are given in Table (II) below:

TABLE (II)

| ΔL 3 h | Composition (3) | Composition (4) |
|---|---|---|
| $M_1$ | 3.32 | 2.34 |
| $M_2$ | 4.09 | 2.92 |
| $M_3$ | 3.53 | 2.98 |
| ΔL | 3.65 | 2.75 |

These results show clearly that a more intense coloration is observed with the composition containing the silicone-containing emulsifying agent in accordance with the invention.

EXAMPLE 3

The aim of this example is to show the critical nature of the alcohol in accordance with the invention.

Two compositions, a composition (5) in accordance with the invention and a comparative composition (6) containing no alcohol as defined in the present invention, were prepared according to the procedure used for composition (1) of Example 1.

| Composition (5): | |
|---|---|
| polydimethylsiloxane sold under the trade name "Silicone Q₂3225C" by Dow Corning | 10% |
| polydimethylsiloxane sold under the trade | 7% |

| | |
|---|---|
| name "Silbione oil 70 047 V 2" by Rhône-Poulenc | |
| dihydroxyacetone | 5% |
| anhydrous dextrose | 2% |
| propylene glycol | 30% |
| demineralized water | qs 100% |
| Composition (6): | |
| polydimethylsiloxane sold under the trade name "Silicone Q₂3225C" by Dow Corning | 10% |
| polydimethylsiloxane sold under the trade name "Silbione oil 70 047 V 2" by Rhône-Poulenc | 7% |
| dihydroxyacetone | 5% |
| anhydrous dextrose | 2% |
| glycerol | 30% |
| demineralized water | qs 100% |

For these two compositions, the comparative test was performed according to the same procedure as for Example 2. The results are given in Table (III) below:

TABLE (III)

| ΔL 3 h | Composition (5) | Composition (6) |
|---|---|---|
| M₁ | 4.34 | 2.03 |
| M₂ | 5.04 | 3.55 |
| M₃ | 4.46 | 3.84 |
| ΔL | 4.63 | 2.80 |

These results show clearly that a more intense coloration is obtained with the composition containing propylene glycol in accordance with the invention.

I claim:

1. A topically applicable cosmetic composition adopted for the artificial tanning of the skin, comprising a cosmetically acceptable water-in-silicone emulsion which comprises:
   (i) an effective artificial tanning amount of dihydroxyacetone (DHA);
   (ii) at least one mono- or dihydric alcohol; and
   (iii) at least one silicone-containing emulsifying agent consisting of a polydimethylsiloxane of formula (I) or (II).

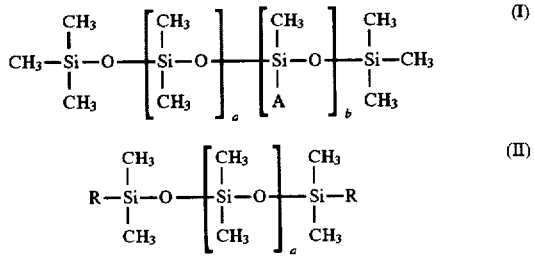

wherein in both formulae (I) and (II):

a is an integer $\geq 1$ and $\leq 500$;

b is an integer $\geq 1$ and $\leq 100$;

R is a radical: $-C_nH_{2n}-(-OC_2H_4)_x-(-OC_3H_6)_4-O-R'$, wherein R' is H or a linear or branched $C_1-C_{12}$ alkyl radical, and:

x is an integer $\geq 0$ and $\leq 50$;

y is an integer $\geq 0$ and $\leq 50$;

$x+y \geq 1$ and n is an integer $\geq 2$ and $\leq 12$.

2. The cosmetic composition of claim 1, where in the silicone-containing emulsifying agent of formula (I) or (II) at least one of a, b, x or y is defined as follows:

$2 \leq a \leq 450$ $2 \leq b \leq 40$ $1 \leq x \leq 30$ $0 \leq y \leq 30$ $y \leq x$.

3. The cosmetic composition according to claim 2, wherein all of a, b, x and y are as defined therein.

4. The cosmetic composition of claim 1, wherein R' is hydrogen.

5. The cosmetic composition according to claim 4, wherein the silicone-containing emulsifying agent contained therein is a polydimethylsiloxane of the following formula:

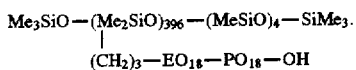

$$(CH_2)_3-EO_{18}-PO_{18}-OH$$

6. The cosmetic composition according to claim 1, wherein the silicone-containing emulsifying agent contained therein is a polydimethylsiloxane of formula (I) or (II) which is dispersed in a volatile polydimethylsiloxane.

7. The cosmetic composition according to claim 1, wherein said alcohol is a dihydric alcohol.

8. The cosmetic composition according to claim 7, wherein said dihydric alcohol is propylene glycol.

9. The cosmetic composition according to claim 1, wherein the mono- or dihydric alcohol comprises at least 2% by weight relative to the total weight of the composition.

10. The cosmetic composition according to claim 1, wherein the mono- or dihydric alcohol ranges from about 10 to 50% by weight relative to the total weight of the composition.

11. The cosmetic composition according to claim 1, wherein the amount of the silicone-containing emulsifying agent ranges from about 0.1 and 20% by weight relative to the total weight of the composition.

12. The cosmetic composition according to claim 1, wherein the amount of the silicone-containing emulsifying agent ranges from about 0.5 to 10% by weight relative to the total weight of the composition.

13. A method for artificially tanning human skin, comprising topically applying thereto an effective amount of the cosmetic artificial tanning composition as defined by claim 1.

14. A method for artificially tanning human skin, comprising topically applying thereto an effective amount of the cosmetic artificial tanning composition as defined by claim 2.

15. A method for artificially tanning human skin, comprising topically applying thereto an effective amount of the cosmetic artificial tanning composition as defined by claim 3.

16. A method for artificially tanning human skin, comprising topically applying thereto an effective amount of the cosmetic artificial tanning composition as defined by claim 4.

17. A method for artificially tanning human skin, comprising topically applying thereto an effective amount of the cosmetic artificial tanning composition as defined by claim 5.

18. A method for artificially tanning human skin, comprising topically applying thereto an effective amount of the cosmetic artificial tanning composition as defined by claim 6.

19. A method for artificially tanning human skin, comprising topically applying thereto an effective amount of the cosmetic artificial tanning composition as defined by claim 7.

20. A method for artificially tanning human skin, comprising topically applying thereto an effective amount of the cosmetic artificial tanning composition as defined by claim 8.

21. A method for artificially tanning human skin, comprising topically applying thereto an effective amount of the cosmetic artificial tanning composition as defined by claim 9.

22. A method for artificially tanning human skin, comprising topically applying thereto an effective amount of the cosmetic artificial tanning composition as defined by claim 10.

23. A method for artificially tanning human skin, comprising topically applying thereto an effective amount of the cosmetic artificial tanning composition as defined by claim 11.

24. A method for artificially tanning human skin, comprising topically applying thereto an effective amount of the cosmetic artificial tanning composition as defined by claim 12.

* * * * *